United States Patent [19]

Malinoff

[11] Patent Number: 4,468,974
[45] Date of Patent: Sep. 4, 1984

[54] PIPETTE SAMPLER AND RELATED APPARATUS

[75] Inventor: Donald Malinoff, Granada Hills, Calif.

[73] Assignee: Culture Tek Corporation, Granada Hills, Calif.

[21] Appl. No.: 307,745

[22] Filed: Oct. 2, 1981

[51] Int. Cl.³ .............................................. B01L 3/02
[52] U.S. Cl. ............................ 73/863.32; 73/864.11; 422/100
[58] Field of Search ........... 73/863.32, 864.02, 864.11, 73/864.15; 422/100

[56] References Cited
U.S. PATENT DOCUMENTS 3,696,971 10/1972 Maclin ........................ 73/863.32 X
3,938,392 2/1976 Rodrigues ...................... 73/864.11
3,982,438 9/1976 Byrd ............................ 73/863.32
4,178,345 12/1979 Terk .............................. 422/61
4,195,060 3/1980 Terk .............................. 422/61

Primary Examiner—S. Clement Swisher
Assistant Examiner—John E. Chapman, Jr.
Attorney, Agent, or Firm—Spensley Horn Jubas & Lubitz

[57] ABSTRACT

An improved pipette device for removing and transferring a plurality of liquid samples to and from a multi-well tray is disclosed. The pipette device comprises the housing having an elongated plate defining a first chamber therein. A patterned array of collector conduits are joined to the plate such that a first outwardly extending section extends into the chamber and a second outwardly extending section, in flow communication with the first, extends away from the chamber and toward the tray. A port is formed on the housing such that a vacuum can be created in the first chamber whereby a predetermined quantity of liquid is caused to flow into each of the collector conduits. The conduits are designed to contain decreasingly smaller volumes to allow precise measure of the contained volume when the conduits are filled.

11 Claims, 4 Drawing Figures

PIPETTE SAMPLER AND RELATED APPARATUS

BACKGROUND OF THE INVENTION

1. Field of the Invention

This invention relates to an improved pipette sampler and related apparatus.

2. Prior Art

The use of various sized and shaped pipettes for withdrawing a liquid sample from a container so as to measure the same and transfer it to a second container is well recognized in the prior art. One problem with such pipettes is that in order to measure and transfer a given quantity of liquid, a great deal of care must be exercised in order to insure accuracy. While this prior art method is satisfactory, in terms of accuracy, it is very time consuming. Recent advances in the microbiological, immunological and other medical laboratory research have made such approach outmoded. This is because such devices may require the container with the liquid to be measured and transferred to be opened to the atmosphere each time the pipette is filled. In many procedures, continued and repeated exposure to the atmosphere can lead to poor results. Further, today mass sampling and testing is done. If individual samples had to be taken, even if there were no adverse consequences, the time factor using this old method would slow research to a snail's pace.

The prior art has recognized this problem, and has come up with a number off different devices which are alleged solutions. These devices are adapted to be used with multi-well trays, with a liquid sample in each well or in a tube disposed in each well. More recent devices are adapted to simultaneously withdraw a relatively large number of samples from the individual tubes or wells which contain the sample. Devices of this type are shown in U.S. Pat. Nos. 3,982,438; 4,158,035; 3,261,208; and 3,568,735. A review of these patents will illustrate that while a solution is provided to the transfer of fluid from multi-well laboratory trays such as are now used extensively in microbiological and immunological laboratory work, they are relatively complex, and thus expensive.

The device and apparatus of the present invention overcomes many problems associated with the prior art in a straightforward manner and without undue complexity or expense.

SUMMARY OF THE INVENTION

The present invention pipette sampler and related apparatus has particular utility in a microbiological laboratory setting such as those used in antibody research, cloning, assay technology and the like. The following broad description of the invention is set forth in a laboratory setting so as to provide some insight into how the device of the present invention can be used. Broadly speaking, the pipette sampler of the present invention is designed to separately remove a predetermined amount of liquid from a 96-well microculture dish or tray, and transfer the volume removed to another 96 well tray in one operation. Such 96-well trays are well known and are used throughout this industry.

In a typical laboratory involved in antibody research, cell fusion is used to produce hybrids which in turn are used to produce antibodies. Antibodies are produced in the supernatant of the cell cultures performed in the 96-well microculture trays. One hundred-fifty microliter cultures are usually established from which 50 microliter alignuts are to be removed periodically and assayed for the production of specific antibodies. This should be accomplished rapidly and effectively to insure sterility of the original cultures which should be maintained after each sampling. Further, the sampler must either be disposable or sterilized to insure the integrity of the research. As stated above, the complexity of the prior art devices is such that they do not appear to be disposable as is the device of the present invention. Further, the complexity would also appear to make their disposal after each use very uneconomic. The device of the present invention can be used in situations where the prior art devices are used, but has the additional benefit of being particularly adapted for use with any microculture system where sampling is required and sterility is to be maintained between each sample taken.

In order to achieve these and other goals, the pipette sampler of the present invention comprises a housing having a top member, side and end members, and a generally flat plate joined to the side and end members which along with the top define a first manifold chamber. A rectilinear array of elongated, outwardly extending collector conduits are disposed on the plate. The collector conduits have a first portion which is configured to be inserted into an associated well on the multi-well tray, and a second portion which extends into the first manifold chamber. The first and second portions have coaxial openings for fluid flow, but the opening for fluid flow in the first portion is larger than the opening for fluid flow in the second portion. A port is provided on the housing in fluid communication with the first chamber whereby a vacuum can be created in the first chamber causing a predetermined amount of liquid to flow into the first portion of each of the collector conduits. Because the openings for fluid flow in the first and second portions are specifically selected, liquid can readily flow into the first portion, but once it reaches the opening in the second portion, little, if any liquid continues to flow into the second portion.

The novel features which are believed to be characteristic of the invention, both as to its organization and method of operation, together with further objectives and advantages thereof, will be better understood from the following description considered in connection with the accompanying drawings in which a presently preferred embodiment of the invention is illustrated by way of example. It is to be expressly understood, however, that the drawings are for the purpose of illustration and description only, and is not intended as a definition of the limits of the invention.

DESCRIPTION OF A PREFERRED EMBODIMENT

Figure 1:
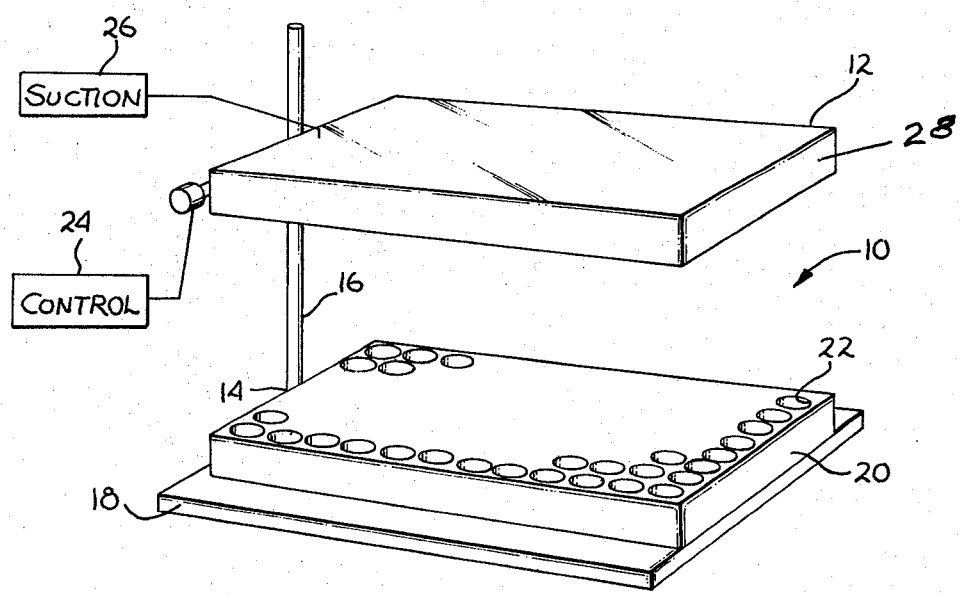
FIG. 1 is a perspective view showing the pipette sampler and related apparatus.

As discussed hereinabove, the present invention is directed to a pipette sampler and related apparatus for removing a plurality of liquid samples from a multi-well tray. Referring to FIG. 1, the entire apparatus 10 is illustrated. The apparatus 10 includes a pipette sampler 12 mounted on a stand 14, and more specifically, on a post 16. Various means can be used to attach sampler 12 to the post 16 including arm members which would extend out from the post, a bracket arrangement and the like. The post 16 is secured to a substantially flat base 18 such that the multi-well tray 20 can be appropriately positioned beneath the sampler 12. Such tray 20 typically has 96 wells, although different numbers of wells are clearly within the scope of the present invention. Into each of these wells 22 a culture can be grown in microliter quantities. Alternately, test tubes could be placed into each of the wells 22 and the liquid placed in each of the tubes. A control member 24 is used to raise and lower the sampler 12 such that it can be positioned directly on top of the tray 20. As more fully described hereinbelow, a suction pump 26 or other similar means for creating a vacuum in the sampler 12 is joined to the sampler 12 such that predetermined quantities of liquid from each of the wells 22 can be withdrawn into the sampler 12. Such samples can then be placed into an empty tray or into a tray in which a different culture or other material is contained.

Figure 2:
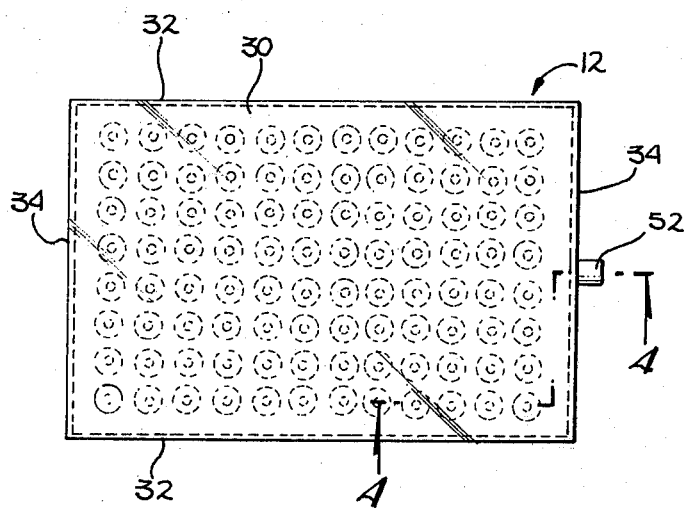
FIG. 2 is a top plan view showing the pipette sampler.
Figure 3:
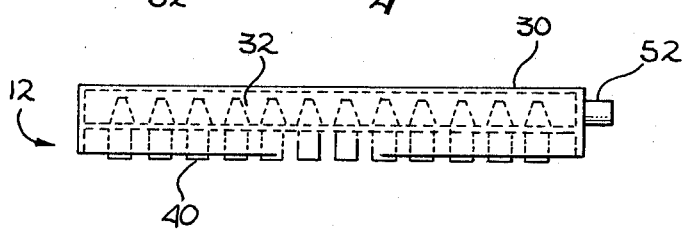
FIG. 3 is a front plan view of the pipette sampler.
Figure 4:
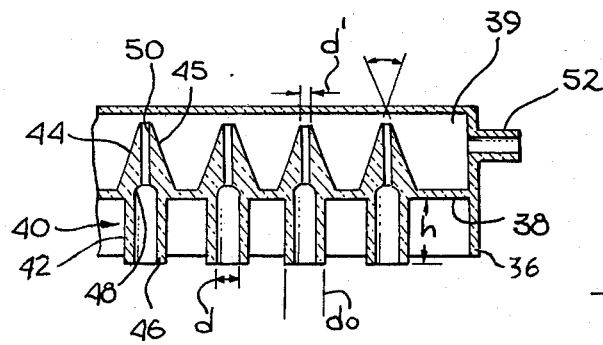
FIG. 4 is a cut-away view of FIG. 2 taken along lines 4—4 and showing the collector conduits in the pipette sampler.

Referring now to FIGS. 2, 3 and 4, the sampler 12 is more clearly illustrated. Sampler 12 is comprised of a clear plastic housing 28 having a generally rectangular configuration. It has a generally flat top 30, flat sides and ends 32, 34, such that a box-like structure is created. A skirt 36 is circumferentially disposed about the housing 28 and is of a configuration so as to matingly engage an associated tray 20. Skirt 36 perferably extends about the sides and ends of the tray 20 such that the samples are exposed as little as possible to the ambient environment during the sampling procedure.

A plate 38 is disposed within the housing 28, and is joined to the sides and ends 32, 34. Plate 38, along with sides and ends 32, 34 and top 30 form a first manifold chamber 39. Extending from plate 38 are a plurality of collector conduits 40. Inasmuch as the usual tray 20 includes 96 wells, 96 collector conduits would be positioned on plate 38. Collector conduits 40 include a first portion 42 and a second portion 44. First portion 42 depends down from the plate 38 and is configured so as to engage an associated well 22 on tray 20. Second portion 44, formed of inclined walls 45, extends up from the plate 38 and into the chamber 39. A first opening 46 is formed in the first portion 42 and has an internal diameter d of approximately 0.088 inches ±20%. The outside diameter of the first portion 42, $d_o$, is approximately 0.22 inches ±20%. It has been found that openings 46 of this size are sufficient to withdraw the desired amount of samples. The second portion 44 defines an opening 50 which has a diameter d' of approximately 0.032 inches ±20%. Thus, opening 50 is substantially smaller than opening 46. Opening 50 is chosen such that filling to the opening 50 provides a precise measurement. Excess filling results in an overflow of liquid into chamber 39, such that the content of collector conduit 40 remains constant thus insuring transfer of a precise volume of liquid. This feature is believed unique to the conical shape design which also prevents mixing of the liquid in adjacent collector conduits 40 when overflow occurs. While the drawings (FIG. 4) show a rounded bottom 48, the internal walls from opening 46 to opening 50 can be tapered, so as to change the shape of bottom 48.

The operation of the apparatus 10 will now be described.

In a typical situation, the sampler 12 would be contained in a sterile package. The package would be opened and the sampler 12 placed directly above the tray 20 so that the 96 collector conduits are each directly above an associated well 22. A suction hose is joined to port 52 in flow communication with chamber 39 and a suction is applied with a 20 ml. syringe withdrawn to 10 ml. In this manner, fluid is drawn up through opening 46. The flow is stopped when the liquid reaches openings 50.

To transfer liquid from the 96-well tray 20, the filled sampler 12 is lowered into another tray 20 and the syringe plunger is depressed to zero. This procedure releases the contained volume into the acceptor tray. Typically, the height of each portion 42 is approximately 0.3 inches and is designed to leave approximately 100 microliters in the tray 20 which is being harvested. In addition, the device can be set on a tray which is not divided into individual wells but contains liquid which is used to feed or to be transferred to 96 microwell plates. The device thus has multiple functions and is unique in its diversity. It can transfer reagents to 96 well microplates. It can also remove a liquid from such plates and accurately transfer a specified volume of liquid to another tray.

After the sample is obtained, the suction hose can be removed and the sampler 12 discarded. Obviously, upon completion of the transfer, the cover can be placed on the tray 20 to avoid contamination. Thus, in this way 96 separate specimens are readily transferred from one tray to another in a straightforward manner and without a complex device such as those shown in the prior art. Further, because the sampler 12 of the present invention is straightforward in its construction, it is particularly adapted to situations where single use is desired.

While this invention has been described in its preferred embodiments, it is to be expressly understood that the words which have been used are words of description rather than of limitation, and that changes within the purview of the appended claims may be made without departing from the true scope and spirit of the invention in its broader aspects.

I claim:

1. A pipette sampler for removing a plurality of liquid samples from a multi-well tray, comprising:
    a generally rectangular housing having a top member, side and end members;
    a generally flat, rectangular plate having a depending skirt integrally formed therewith, said plate along with said top, side and end members of said housing defining a first chamber;
    a patterned array of microliter collector conduits integrally formed on said plate, each said conduit having a first lower portion and second upper coaxial portion, said second upper portion in flow communication with said first chamber and having inclined walls integral with and extending away from said plate, and said first lower portion depending away from said second portion and said plate, and configured for insertion into said multi-well tray; and further wherein the area for fluid flow in said first portion is larger than the area for fluid flow in said second portion, and the opening for fluid in said second portion is sized such that precise filling of each said conduit is encouraged while substantially precluding fluid from overflowing out of said conduit in said housing; and means for forming a vacuum in said first chamber whereby a predetermined quantity of liquid flows into each said collector conduit.

2. A pipette sampler according to claim 1 wherein said housing is integrally formed with said plate.

3. A pipette sampler according to claim 1 wherein said sampler is made of plastic.

4. A pipette sampler according to claim 1 wherein said vacuum forming means comprises a port in flow communication with said first chamber.

5. The pipette sampler according to claim 1 wherein the internal diameter for flow in said first portion is about 0.88 inches ±20%.

6. A pipette sampler for removing a plurality of liquid samples from a multi-well tray, comprising:

an integral, one-piece housing having a top member, and side and end members;

a generally flat plate integrally formed with said side and end members, said plate along with said top, side and end members defining a first manifold chamber;

a matrix array of elongated microliter collector conduits with a first portion of each conduit extending from a first side of said plate and configured to be inserted into an associated well on said multi-well tray, and a second portion extending from a second, opposite side of said plate into said first manifold chamber, said first and second portions having co-axial openings for fluid flow, said opening for fluid flow in said first portion being larger than said opening for fluid flow in said second portion, and said opening for fluid flow in said second portion being sized such that precise filling of each said conduit is encouraged while substantially precluding fluid from overflowing out of said conduit into said housing; and a port on said housing in flow communication with said first chamber whereby a vacuum can be created in said first chamber causing a predetermined quantity of liquid to flow into each said collector conduit.

7. A pipette sampler according to claim 6 wherein said second portion of each said collector conduit has inclined walls integrally formed with and extending away from said plate.

8. The pipette sampler according to claim 6 wherein the internal diameter for flow in said first portion is about 0.88 inches ±20%.

9. In a pipette sampler apparatus having a multi-well tray and means for mounting said sampler apparatus adjacent said tray, the improvement wherein said sampler apparatus comprises a generally rectangular, integral housing having a top member, side and end member;

a generally rectangular flat plate integrally formed with said side and end members, said plate along with said top, side and end members defining a first manifold chamber;

a matrix array of elongated, microliter collector conduits integrally formed on said plate with a first portion of each conduit configured to be inserted into an associated well on said multi-well tray, and a second portion extending into said first manifold chamber, said first and second portions have co-axial openings for fluid flow, and wherein the opening for fluid flow in said first portion is larger than the opening for fluid flow in said second portion, and the opening for fluid flow in said second portion is sized such that precise filling of each said conduit is encouraged while substantially precluding fluid from overflowing said conduit into said housing, and a port on said housing in flow communication with said first chamber whereby a vacuum can be created in said first chamber causing a predetermined quantity of liquid to flow into each said collector conduit.

10. An apparatus according to claim 9 further including a suction pump joined to said port for forming a vacuum in said first chamber.

11. The pipette sampler according to claim 9 wherein the internal diameter for flow in said first portion is about 0.88 inches ±20%.

* * * * *